United States Patent
Zhong et al.

(10) Patent No.: US 9,775,868 B2
(45) Date of Patent: Oct. 3, 2017

(54) TRADITIONAL CHINESE MEDICINE COMBINATION FOR REGULATING IMMUNE FUNCTION AND PREPARATION METHOD THEREFOR

(71) Applicant: JIANGZHONG PHARMACEUTICAL CO., LTD., Nanchang, Jiangxi (CN)

(72) Inventors: Hongguang Zhong, Nanchang (CN); Minzhi Yi, Nanchang (CN); Jianzhong Lu, Nanchang (CN)

(73) Assignee: JIANGZHONG PHARMACEUTICAL CO., LTD., Nanchang, Jiangxi (CN)

( * ) Notice: Subject to any disclaimer, the term of this patent is extended or adjusted under 35 U.S.C. 154(b) by 14 days.

(21) Appl. No.: 14/428,313

(22) PCT Filed: Sep. 22, 2013

(86) PCT No.: PCT/CN2013/001113
§ 371 (c)(1),
(2) Date: Mar. 13, 2015

(87) PCT Pub. No.: WO2014/040396
PCT Pub. Date: Mar. 20, 2014

(65) Prior Publication Data
US 2015/0265664 A1    Sep. 24, 2015

(30) Foreign Application Priority Data
Sep. 13, 2012   (CN) .......................... 2012 1 0336446

(51) Int. Cl.
| | |
|---|---|
| A61K 36/00 | (2006.01) |
| A61K 36/074 | (2006.01) |
| A61K 36/896 | (2006.01) |
| A61K 36/8964 | (2006.01) |
| A61K 36/068 | (2006.01) |
| A61K 36/258 | (2006.01) |
| A61K 36/344 | (2006.01) |
| A61K 36/481 | (2006.01) |
| A61K 36/738 | (2006.01) |
| A61K 9/48 | (2006.01) |
| A61K 9/16 | (2006.01) |

(52) U.S. Cl.
CPC .......... *A61K 36/074* (2013.01); *A61K 9/1688* (2013.01); *A61K 9/4833* (2013.01); *A61K 36/068* (2013.01); *A61K 36/258* (2013.01); *A61K 36/344* (2013.01); *A61K 36/481* (2013.01); *A61K 36/738* (2013.01); *A61K 36/896* (2013.01); *A61K 36/8964* (2013.01); *A61K 2236/19* (2013.01)

(58) Field of Classification Search
None
See application file for complete search history.

(56) References Cited

U.S. PATENT DOCUMENTS

| | | | |
|---|---|---|---|
| 2003/0077339 A1* | 4/2003 | Yoon et al. ................... 424/725 |
| 2010/0291154 A1 | 11/2010 | Han et al. | |

FOREIGN PATENT DOCUMENTS

| | | | | |
|---|---|---|---|---|
| CA | WO 9930725 A1 * | 6/1999 | ........... A61K 36/258 |
| CN | 1413647 A | 4/2003 | |
| CN | 1552437 A * | 12/2004 | |
| CN | 1868251 A * | 11/2006 | |
| CN | 101273780 | 10/2008 | |
| CN | 101292742 A | 10/2008 | |
| CN | 101536968 A * | 9/2009 | |
| CN | 101612182 A * | 12/2009 | |
| CN | 101999663 A | 4/2011 | |
| CN | 102228252 A | 11/2011 | |
| CN | 102274258 A | 12/2011 | |
| CN | 102274259 A | 12/2011 | |
| CN | 102283340 | 12/2011 | |
| CN | 102406163 A | 4/2012 | |
| CN | 102526606 | 7/2012 | |
| JP | H08157388 A | 6/1996 | |
| JP | 2001103933 | 4/2001 | |
| JP | 2004099613 A | 4/2004 | |

(Continued)

OTHER PUBLICATIONS

Wang, Mangiferin, an anti-HIV-1 agent targeting protease and effective against resistant strains. Molecules (Basel, Switzerland), (2011) vol. 16, No. 5, pp. 4264-4277.*

(Continued)

*Primary Examiner* — Qiuwen Mi
(74) *Attorney, Agent, or Firm* — Loza & Loza, LLP; Michael F. Fedrick

(57) ABSTRACT

The present invention relates to a traditional Chinese medicine composition for regulating immunity and preparation method thereof, characterized in that the composition comprises raw materials such as Radix Panacis Quinquefolii, *Ganoderma*, fermented *Cordyceps sinensis* powder, Flos Rosae Rugosae, and Rhizoma Anemarrhenae and is prepared into various conventional pharmaceutical formulations through processes such as pulverization, water decoction and alcohol extraction. The traditional Chinese medicine composition is effective in preventing and treating allergic diseases, hepatitis B and AIDS, elevating leukocytes, preventing and treating radiation injury, reducing toxic and side effects resulting from radiotherapy and chemotherapy, improving the male sexual function, enhancing immunity of the human body and alleviating physical fatigue.

18 Claims, No Drawings

(56) References Cited

FOREIGN PATENT DOCUMENTS

| JP | 2007045713 A | 2/2007 |
|---|---|---|
| JP | 2011506308 | 3/2011 |
| KR | 20100137223 A | 12/2010 |

OTHER PUBLICATIONS

Skin disorder from Merck Manual, pp. 1-2, Accessed Feb. 3, 2009.*
Vitiligo from Merck Manual, pp. 1-2, Accessed Feb. 3, 2009.*
Viral disease from Wikipedia, pp. 1-9, Accessed Dec. 16, 2016.*
Walker, Personality, coping and sex as psychosocial aspects of psoriatic arthropathy, Dermatology and Psychosomatics, (2003) vol. 4, No. 1, pp. 27-32.*
Yu et al, Effects of long-term oral administration of polymeric microcapsules containing tyrosinase on maintaining decreased systemic tyrosine levels in rats, Journal of pharmaceutical sciences, (Apr. 2004) vol. 93, No. 4, pp. 831-837.*
Cleaver, Defective repair replication of DNA in xeroderma pigmentosum, Nature [London], (1968) vol. 218, No. 5142, pp. 652-656.*
Granger et al, Association between dietary fat and skin cancer in an Australian population using case-control and cohort study designs, BMC Cancer (2006), 6: 1-7.*
Huang, Yanping, "Research status of Bulbus Lilii", China Pharmaceuticals, China Academic Journal Electronic Publishing House (2010), 4 pages.
Wang et al, "Pharmacological Functions of Chemicals in Rhizoma Anemarrhenae", China Academic Journal Electronic Publishing House (2010), 110-115.
Xu, Aijuan et al., "Research development of Rhizoma Anemarrhenae", China Academic Journal Electronic Publishing House (2008), 6 pages.
International Search Report for PCT/CN13/01113 dated Dec. 5, 2013; 1 page.
First office action for counterpart Chinese Patent Application No. 201210336446.2, Dec. 29, 2015.
Search report for counterpart Chinese Patent Application No. 201210336446.2, Dec. 29, 2015.
First office action for counterpart Chinese Patent Application No. 201210336446.2, Dec. 29, 2015, with English translation.
Extended European Search Report for 13837349.3 dated May 2, 2016; 10 pages.
WPI/Thomson "Medicinal composition comprises (in parts by wt.): water and/alcohol extract as active components, and additives composed of ginseng and/or American ginseng (5-150), *Ganoderma lucidum* (5-160), and fermented Cordyceps sinensispowder (1-90)", Thomson Scientific. Week 201219 London. AN 2012-A22889; XP002756407 (referencing Chinese Patent Application No. 102274259, published Dec. 14, 2011).
WPI/Thomson "Medicinal composition comprises (in parts by wt.): water and/or alcohol extract as active components, and additives composed of ginseng and/or American ginseng (5-150), *Ganoderma lucidum* (5-160), Cordyceps sinensis(1-120) and/or fermented Cordyceps sinensispowder (1-90)", Thomson Scientific. Week 201220 London. AN 2012-A22891, XP002756408 (referencing Chinese Patent Application No. 20111208868, corresponding to International Patent Publication No. WO2013013501, published Jan. 31, 2013).
WPI/Thomson "A health care food composition comprises (pts.wt.) American ginseng (10-50), *Ganoderma lucidum*(10-50) and fermented Cordyceps sinensis(10-50)", Thomson Scientific. Week 200909 London. AN 2009-B33845; XP002756409 (referencing Chinese Patent Publication No. 101292742, published May 30, 2012).
WPI/Thomson "A kind of Radix Panacis Quinquefolii Flos Rosae Rugosae buccal tablet/A Chinese medicine health Droduct with fatigue resisting and immunity improving effects", Jan. 22, 2008 (Jan. 22, 2008), XP002756410 (referencing Chinese Patent No. CN101757158, published Jun. 30, 2010).
Durairaj et al, "Quantitative augmentation of immune cells in elderly normal mice by short-term, daily consumption of an extract of North American ginseng (*Panax quinquefolius*)", Biomedical Research (India) 2013 Scientific Publishers of India IND, vol. 24, No. 2, Mar. 20, 2013 (Mar. 20, 2013), pp. 199-205, XP009189493, ISSN: 0970-938X.
Yamaguchi et al "Augmentation of various immune reactivities of tumor-bearing hosts with an extract of Cordyceps sinensis", Biotherapy, Kluwer Academic Publishers, Dordrecht, NL, vol. 2, No. 3, Jan. 1, 1990 (Jan. 1, 1990), pp. 199-206, XP001069490, ISSN: 0921-299X, DOI: 10.1007/BF02173520.
Guerrero-Analco et al, "Bioactive Polysaccharides of North American Ginseng *Panax quinquefolius* L. in Modulation of Immune Function: Preliminary Chemical and Biological Characterization", Planta Medica, Thieme Verlag, DE, vol. 79, No. 10, Jul. 1, 2013 (Jul. 1, 2013), pp. 835-836, XP009189492, ISSN: 0032-0943.
Yue et al, "Immunomodulatory Activities of Ganoderma sinense Polysaccharides in Human Immune Cells", Nutrition and Cancer. Routledge. US. vol. 65. No. 5. Jul. 1, 2013 (Jul. 1, 2013). pp. 765-774. XP009189488. ISSN: 0163-5581.
Yang et al, "Effects of *Ganoderma lucidum* essence powder and *Ganoderma Lucidum* spore powder on immune function of mice with Lewis lung cancer", Chinese Journal of Biologicals/Chinese Preventive Medicine Association. China. vo 1. 25. No. 9. Sep. 1, 2012 (Sep. 1, 2012). pp. 1171-1175. XP009189495. ISSN: 1004-5503.
Translation of Chinese Patent Publication No. 101292742, published May 30, 2012.
Translation of Chinese Patent Publication No. 102274259, published Dec. 14, 2011.
Translation of Chinese Patent Publication No. 102274258, published Dec. 14, 2011.
Second Office Action issued on Jul. 11, 2016 for counterpart Chinese patent application No. 201210336446.2.
Examination Report for counterpart European patent application No. 13837349.3 issued on Jan. 13, 2017.
Second Office Action issued for corresponding Russian Patent Application No. 2015113319 mailed on Jan. 19, 2017 with the English translation.
Korean Patent Appln. No. 10-2015-7008510. Office Action (dated Jun. 20, 2017).
Japanese Patent Appln. No. 2015-531424. Office Action (dated May 16, 2017).
Wang et al., "Pharmacological functions of chemicals in rhizoma anemarrhenae." Science & Technology Review, vol. 28, No. 12, pp. 110-115 (2010).
Huang, "Research Status of Lily," China Pharmaceuticals & Healthcare Report, vol. 19, No. 8, pp. 88, I, II (2010).
Chai, "Inhibitory Effects of Several Korean Traditional Herbs on Anaphylactic Reaction and Mast Cell Activation." Korean J. Microscopy, vol. 4:4 (2010).

* cited by examiner

TRADITIONAL CHINESE MEDICINE COMBINATION FOR REGULATING IMMUNE FUNCTION AND PREPARATION METHOD THEREFOR

CROSS-REFERENCE TO RELATED APPLICATIONS

This application is the U.S. national stage of International Patent Application No. PCT/CN2013/001113, filed on Sep. 22, 2013 and entitled TRADITIONAL CHINESE MEDICINE COMBINATION FOR REGULATING IMMUNE FUNCTION AND PREPARATION METHOD THEREFOR, which claims the benefit of priority under 35 U.S.C. §119 from Chinese Patent Application No. 201210336446.2, filed Sep. 13, 2012. The disclosures of the foregoing applications are incorporated herein by reference in their entirety.

TECHNICAL FIELD

The present invention relates to a traditional Chinese medicine composition for regulating immunity and a preparation method thereof.

BACKGROUND

The immune system is a self defense mechanism to protect the body, and plays an important role in the occurrence, development, and prevention of diseases. In view of modern immunology, the immunity of the human body has three major effects, i.e., protection from infection, homeostasis, and immune surveillance. Under normal circumstances, the body maintains an equilibrium state, and relies on immunity to resist various infections and remove harmful substances from the body, i.e., "self-identification" and "exclusion of foreign substances", so as to achieve homeostasis and a physiologically protective effect. However, when the immune system is dysfunctional, the homeostasis is disrupted, which leads to a variety of autoimmune diseases, such as rheumatoid arthritis, lupus, scleroderma, Behcet's disease, AIDS and other diseases, and is also closely related to the occurrence of diseases such as cancer, hypertension, and diabetes.

In traditional Chinese medicine, the effects to maintain the normal function of the body and to resist and remove various harmful factors are called "vital qi", while those harmful factors are called "pathogenic qi". "Vital qi" corresponds to the body's immunity. "Pathogenic qi" is classified into "external pathogenic qi" and "internal pathogenic qi", that is, various pathogenic factors. "With vital qi present in the body, pathogenic factors have no impact", which indicates that external pathogenic factors can be blocked by normal immunity in the body and, even if they invade the human body, can be eradicated. "When pathogens prevail, qi must have been deficient", which indicates that, if immunity is deficient, normal physiological functions are impaired and a disease may occur. In traditional Chinese medicine, it is believed that the occurrence, development, and transformation of diseases depend on the balance between vital qi and pathogenic qi, which is closely related to the immunity of the body, and a principal therapeutic protocol, "strengthening vital qi to eliminate pathogenic factors", is thus proposed. Most traditional Chinese medicines are natural drugs having a mild nature and few adverse effects as well as unique efficacy in coordinating the overall balance of the body and enhancing the body resistance against diseases. Modern scientific researches have proved that more than 200 traditional Chinese medicines such as Radix Et Rhizoma Ginseng, Radix Astragali, *Ganoderma*, Fructus Lycii, Radix Isatidis, and Flos Lonicerae that are effective in strengthening vital qi or eliminating pathogenic qi function well in immunoregulation and can regulate various aspects of immunity.

The traditional Chinese medicine composition (TCM composition) of present invention comprising raw materials such as Radix Panacis Quinquefolii, *Ganoderma*, fermented *Cordyceps sinensis* powder, Flos Rosae Rugosae, Rhizoma Anemarrhenae, Bulbus Lilii is formulated and optimized through clinical and experimental studies on the basis of clinical experience in combination with modern research results. Such a composition has functions of invigorating Qi and nourishing Yin, benefiting kidney and invigorating lung, regulating Qi flowing and expelling blood stasis, clearing heat and moistening lung, strengthening vital qi and eliminating pathogens, as well as regulating immunity. As demonstrated by the clinical studies, the TCM composition of the present invention can enhance the immunity of the body, has superior efficacy against allergic diseases including allergic rhinitis, allergic asthma, atopic dermatitis and urticaria, and viral diseases including hepatitis B and AIDS, and is capable of increasing white blood cells, preventing and treating radiation injury, and reducing toxic and side effects resulting from chemotherapy.

SUMMARY OF THE INVENTION

The present invention aims to provide a traditional Chinese medicine composition (TCM composition) for regulating immunity and a preparation method thereof, which composition has the effects of invigorating Qi and nourishing Yin, benefiting kidney and invigorating lung, regulating Qi flowing and expelling blood stasis, clearing heat and moistening lung, strengthening vital qi and eliminating pathogens, as well as regulating immunity. This composition is suitable for prevention and treatment of allergic diseases including allergic rhinitis, allergic asthma, atopic dermatitis and urticaria, and viral diseases including hepatitis B and AIDS, and is also capable of increasing leukocytes, preventing and treating radiation injury, reducing the toxic and side effects resulting from chemotherapy, and improving male sexual function.

The technical solutions of the present invention are described as follows.

A TCM composition for regulating immunity is characterized in that it is formulated on the basis of the treatment principle of "strengthening vital qi and eliminating pathogenic qi" in traditional Chinese medicine. The sovereign drug in the formulation, Radix Panacis Quinquefolii, has a bitter yet slightly sweet taste and a cold nature, with effects of invigorating Qi and nourishing Yin, clearing fire and promoting fluid production. Modern scientific researches show that Radix Panacis Quinquefolii has a wide range of biological activities, and have primary active components of Radix Panacis Quinquefolii polysaccharides, saponins and other compounds and trace elements, and can function in a variety of immune cells and promote the secretion of certain cytokines to further exert immunomodulatory effects. Radix Panacis Quinquefolii has a significant protective effect against compromised immunity resulting from immunosuppressants, and thus can have very good adjuvant therapeutic effects on clinical cancer patients on radiotherapy, patients with chronic radiation sickness, and patients with compromised immunity caused by various factors. Radix Panacis Quinquefolii can significantly prolong the swimming time of burdened mice and improve the physical stamina in mice with a dose-response relationship. Further, Radix Panacis Quinquefolii can significantly reduce liver glycogen consumption in mice after exercise, increase liver glycogen reserves, and maintain blood glucose levels during exercise. Radix Panacis Quinquefolii can reduce lactic acid content, increase aerobic metabolic capacity of mice, and suppress the lactic acids produced during glycolysis from accumulating in muscles, thereby delaying the occurrence of fatigue. Also, Radix Panacis Quinquefolii can lower the serum urea nitrogen content during exercise, enhancing the adaptation of the body to the load in exercise and accelerating the relief of fatigue.

The minister drugs, i.e. *Ganoderma* and *Cordyceps*, assist the sovereign drug Radix Panacis Quinquefolii in invigorating Qi and nourishing Yin, as well as in benefiting kidney and invigorating lung. Among these two drugs, *Ganoderma* has a sweet taste, a plain nature, and effects of invigorating Qi and nourishing blood, relieving cough and inhibiting asthma, as well as nourishing heart for tranquilization. Modern scientific researches show that the immunomodulatory function of *Ganoderma* is primarily effected by *Ganoderma* polysaccharides. *Ganoderma* polysaccharides can significantly enhance immunity, for example, by enhancing delayed hypersensitivity in mice, promoting proliferation of lymphocytes, enhancing the cytotoxic cell function, enhancing phagocytosis by macrophages, enhancing the cytotoxic activity of NK cells and promoting cytokine production. Also, *Ganoderma* polysaccharides are effective in relieving fatigue and improving exercise performance. Intragastric administration of *Ganoderma* polysaccharides in mice can significantly prolong the swimming time before exhaustion and anoxia resistance time for mice, increase liver glycogen levels, and reduce the blood lactic acid and blood urea nitrogen levels after highly intense exercises with a quantitative load. *Cordyceps* has a sweet taste and a warm nature, and also has effects of benefiting kidney and invigorating lung, as well as stanching bleeding and dissipating phlegm. Modern researches show that *Cordyceps* is significantly effective in enhancing the immunity of the body, and may significantly increase the mass of thymus and spleen after immunosuppression with dexamethasone, enhance the organ index, and protect liver from immunological injuries. Extracts of *Cordyceps* mycelium and *Cordyceps* fruiting body may enhance the immunity of the body by promoting proliferation of T and B lymphocytes, lowering alloantigen-induced delayed hypersensitivity and mixed lymphocyte reaction, preventing Lewis lung carcinoma in mice, preventing radiation damage, activating the monocyte-macrophage system and improving immunity, in particular increasing the level of humoral immunity. Water extracts of *Cordyceps* can promote proliferation of immune cells, and *Cordyceps* fermentation fluid has a similar function in regulating immunity to that of natural *Cordyceps* fruiting body and artificial *Cordyceps* mycelia.

The assistant and envoy drugs, i.e. Flos Rosae Rugosae and Rhizoma Anemarrhenae, are effective in regulating Qi flowing and resolving stagnation, nourishing yin and moistening dryness, as well as in strengthening vital qi and eliminating pathogenic qi, and they assist the minister drugs in anti-inflammation and immunoregulation. Among these two, Flos Rosae Rugosae has a sweet yet slightly bitter taste and a warm nature, and also has effects of activating Qi flowing and resolving stagnation, as well as activating blood and resolving masses. Modern pharmacological studies show that Flos Rosae Rugosae has a wide range of pharmacological effects, especially in the treatment of cardiovascular diseases and immunological inflammations, and in anti-tumor, anti-oxidation, promotion of bile flow, detoxification, and the like Rhizoma Anemarrhenae has a sweet yet slightly bitter taste and a cold nature, and also has effects of clearing heat-fire as well as nourishing yin and moistening dryness. Modern pharmacological studies have shown that Rhizoma Anemarrhenae has anti-inflammatory, antioxidant, anti-viral, anti-tumor and immunomodulatory effects, in which the active ingredient mangiferin can increase the number of aged red blood cells which in turn can increase IL-2 secretion by T lymphocytes and improve the immunity level of the body, similar to the results of enhancing lymphocyte cytokine secretion by red blood cells. This effect may be partly associated with the activities of mangiferin in resisting lipid peroxidation and stabilizing erythrocyte membrane receptors.

The aforementioned drugs are used in combination to achieve the synergistic effects of invigorating Qi and nourishing Yin, benefiting kidney and invigorating lung, activating Qi flowing and resolving stagnation, removing fever and moistening lung, as well as strengthening vital qi and eliminating pathogenic qi. As shown by modern pharmacological studies, all of the above drugs have anti-inflammatory and immunomodulatory effects to various extents. These drugs are used dialectically according to the theory of traditional Chinese medicine (TCM) with coordination of and reference to Western medicine, and are mutually reinforcing each other.

According to the principle of efficacy-equivalent substitution in TCM prescriptions, in the above TCM composition, the Qi-supplementing drug Radix Panacis Quinquefolii can be substituted with other Qi-supplementing drugs in the same category, such as any one of Radix Et Rhizoma Ginseng, Radix Codonopsis, Radix Pseudostellariae or Radix Astragali, or any one of a Radix Et Rhizoma Ginseng extract, a Radix Codonopsis extract, a Radix Pseudostellariae extract or a Radix Astragali extract; the Yang-supplementing drug, fermented *Cordyceps sinensis* powder, can be substituted with *Cordyceps* or a *Cordyceps* extract. Furthermore, addition of *Ganoderma* spore powder and/or *Ganoderma* spore oil in the TCM composition can improve the immunomodulatory effect of *Ganoderma*.

A TCM composition for regulating immunity is characterized in that it comprises the following raw materials and is prepared from these raw materials in the following parts by weight: 1 to 100 parts of Radix Panacis Quinquefolii, 1 to 100 parts of *Ganoderma*, 1 to 60 parts of fermented *Cordyceps sinensis* powder, 1 to 60 parts of Flos Rosae Rugosae, and 1 to 60 parts of Rhizoma Anemarrhenae.

The TCM composition as stated above, is characterized in that the raw materials in parts by weight are: 10 to 90 parts of Radix Panacis Quinquefolii, 10 to 90 parts of *Ganoderma*, 5 to 50 parts of fermented *Cordyceps sinensis* powder, 5 to 50 parts of Flos Rosae Rugosae, and 5 to 50 parts of Rhizoma Anemarrhenae.

The TCM composition as stated above, is characterized in that the raw materials in parts by weight are: 30 parts of Radix Panacis Quinquefolii, 40 parts of *Ganoderma*, 20 parts of fermented *Cordyceps sinensis* powder, 25 parts of Flos Rosae Rugosae, and 16 parts of Rhizoma Anemarrhenae.

The TCM composition as stated above, is characterized in that, 10 to 50 parts of Bulbus Lilii, or Bulbus Lilii extract prepared from Bulbus Lilii by using a pharmaceutically conventional method in an amount of equivalent crude Bulbus Lilii, is further added into the raw materials, so as to enhance the fatigue-relieving, anoxia resistant, anti-tumor and immunomodulatory effects. Bulbus Lilii has a sweet taste and a slightly cold nature, and has effects of moistening lung for relieving cough as well as clearing heart for tranquilization. Modern pharmacological studies show that Bulbus Lilii is effective in fatigue relieving, anoxia resistance, anti-tumor and immunoregulation; its active component, Bulbus Lilii polysaccharides, has a variety of physiological functions in: 1) anti-oxidation and relieving fatigue (crude polysaccharides of Bulbus Lilii have an anti-oxidation effect and can increase the activity of SOD, catalase and glutathione peptidase in the blood from aging mice induced by D-galactose), 2) free-radical scavenging and anti-aging action (in contrast to common antioxidants (thiourea, ascorbic acid, benzoic acid, etc.) with regard to the ability of hydroxyl free radical scavenging, Bulbus Lilii extract shows a significantly superior scavenging effect), 3) improving immunity and anti-tumor effect (the Bulbus Lilii polysaccharides can enhance non-specific and specific immunity in immunosuppressed mice), and 4) hypoglycemic action (Bulbus Lilii polysaccharides have an substantial hypoglycemic effect in diabetic model mice induced by alloxan).

The TCM composition as stated above, is characterized in that the Radix Panacis Quinquefolii can be substituted with any one of Radix Et Rhizoma Ginseng, Radix Codonopsis, Radix Pseudostellariae or Radix Astragali, or any one of a Radix Et Rhizoma Ginseng extract, a Radix Codonopsis extract, a Radix Pseudostellariae extract or a Radix Astragali extract, and that the fermented *Cordyceps sinensis* powder can be substituted with *Cordyceps* or a *Cordyceps* extract.

The TCM composition as stated above, is characterized in that 10 to 50 parts of *Ganoderma* spore powder and/or *Ganoderma* spore oil may be further added into the raw materials.

The TCM composition as stated above, is characterized in that the fermented *Cordyceps sinensis* powder is prepared through biological fermentation, and the strain from which the fermented *Cordyceps sinensis* powder is derived includes *Paecilomyces hepialli* Chen et Dai, sp. nov, *Mortiscrslla hepialid* C. T. & B. liu, *Synnematium sinensis* Yin & Shen, *Gliocladium roseum* (link) Thom, *Mortierella* sp., *Cephalosporium sinensis* Chen sp. nov, or *Hirsutella sinensis* Liu, Guo, Yu-et Zeng, sp. nov.

The TCM composition as stated above, is characterized in that the source of the raw materials can be crude TCM drugs or extracts prepared by using a pharmaceutically conventional method in an amount of equivalent crude drugs, e.g. a Radix Panacis Quinquefolii extract, a *Ganoderma* extract, a Flos Rosae Rugosae extract, a Rhizoma Anemarrhenae extract, or a Bulbus Lilii extract.

The TCM composition as stated above, is characterized in that the raw materials can be active ingredients extracted in an amount of equivalent crude TCM drugs, such as Radix Panacis Quinquefolii saponins and/or Radix Panacis Quinquefolii polysaccharides, *Ganoderma* polysaccharides and/or *Ganoderma* triterpenoids, *Cordyceps* polysaccharides and/or *Cordyceps* amino acids, Flos Rosae Rugosae flavone and/or Flos Rosae Rugosae oil, and Rhizoma Anemarrhenae saponin and/or mangiferin.

The TCM composition as stated above, is characterized in that it is prepared by a preparation method according to a pharmaceutically conventional process by using pharmaceutically acceptable carrier(s) or excipient(s).

The TCM composition as stated above, characterized in that its preparation method can be any one of the following five processes:

(1) raw materials of the TCM composition in parts by weight as described above are weighed out, dried at 60 to 80° C., pulverized into fine powder of 40 to 100 meshes, and then encapsulated to obtain capsules; or made into water pills, dried at 60 to 80° C., and packed to obtain the final product;

(2) raw materials of the TCM composition in parts by weight as described above are weighed out, into which water in an amount of 6 to 12 folds is added, soaked for 20 to 60 min, and then decocted 1 to 3 times by heating with each decoction lasting for 1 to 2 h; decoctions are combined and subjected to filtration, and the filtrate is concentrated to an appropriate amount; the concentrate is cooled and subjected to high-speed centrifugation to remove impurities, and then prepared, alone or together with pharmaceutically acceptable auxiliaries, into a final formulation;

(3) raw materials of the TCM composition in parts by weight as described above are weighed out, a volatile oil is extracted from Flos Rosae Rugosae, and an aqueous solution obtained after distillation is collected in another container and stored until use; Radix Panacis Quinquefolii and Rhizoma Anemarrhenae are added into 60 to 80% ethanol and extracted twice, the ethanol solutions are combined and filtered, the filtrate is concentrated upon recovery of ethanol, and a first concentrate having a relative density of 1.10 to 1.15 at 60° C. is obtained and stored until further use; *Ganoderma* and fermented *Cordyceps sinensis* powder are mixed with the Flos Rosae Rugosae residue, the Radix Panacis Quinquefolii residue and the Rhizoma Anemarrhenae residue, into which water in an amount of 6 to 12 folds is added, and the mixture is decocted 2 to 3 times; the decoctions are combined with the above aqueous solution and subjected to filtration; the filtrate is concentrated to a relative density of 1.15 to 1.20 at 60° C., uniformly mixed with the first concentrate, and then granulated and dried; the Flos Rosae Rugosae volatile oil is sprayed uniformly to the granules, and mixed uniformly to prepare the final formulation;

(4) raw materials of the TCM composition in parts by weight as described above are weighed out, a volatile oil is extracted from Flos Rosae Rugosae, an aqueous solution obtained after distillation is collected in another container, and the residue together with *Ganoderma* and fermented *Cordyceps sinensis* powder is decocted 2 times with addition of water in an amount of 6 to 12 folds; the decoctions are combined with the above aqueous solution and filtered, and the filtrate is concentrated to a relative density of 1.15 to 1.20 at 60° C.; the concentrate is uniformly mixed with Radix Panacis Quinquefolii extract and Rhizoma Anemarrhenae extract in an amount equivalent to the prescribed amount, and then granulated and dried; the Flos Rosae Rugosae volatile oil is sprayed uniformly to the granules, and mixed uniformly to prepare the final formulation;

(5) extracts or active ingredients are respectively weighed out in an amount of equivalent crude TCM drugs in accordance with the raw materials of the TCM composition in parts by weight, and then prepared into a final formulation with pharmaceutically acceptable carrier(s) or excipient(s) by a pharmaceutically conventional process.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, is characterized in that the final formulation may be a granule, a tablet, a capsule, an electuary, a dripping pill, a pill, powder, a lozenge, a fluid extract, an extract, an injection, a syrup, or an oral liquid.

The TCM composition as stated above, is characterized by its use in the manufacture of a health care food or medicament for preventing and treating allergic diseases, wherein the allergic diseases include allergic rhinitis, allergic asthma, atopic dermatitis, and/or urticaria.

The TCM composition as stated above, is characterized by its use in the manufacture of a health care food or medicament for preventing and treating viral diseases, wherein the viral diseases include hepatitis B and AIDS.

The TCM composition as stated above, is characterized by its use in the manufacture of a health care food or medicament that is effective in elevating leukocytes.

The TCM composition as stated above, is characterized by its use in the manufacture of a health care food or medicament for preventing and treating radiation injury.

The TCM composition as stated above, is characterized by its use in the manufacture of a health care food or medicament for reducing toxic and/or side effects resulting from radiotherapy and chemotherapy.

The TCM composition as stated above, is characterized by its use in the manufacture of a health food or medicament for improving the male sexual function.

The TCM composition as stated above, is characterized by its use in the manufacture of a health food or medicament for enhancing immunity of the human body.

The TCM composition as stated above, is characterized by its use in the manufacture of a health food or medicament for alleviating physical fatigue.

The present invention has the following advantages: a TCM composition for regulating immunity and a preparation method thereof are provided; the TCM composition is effective in invigorating Qi and nourishing Yin, benefiting kidney and invigorating lung, regulating Qi flowing and resolving stagnation, clearing heat and moistening lung, strengthening vital qi and eliminating pathogenic qi, as well as regulating immunity, suitable for prevention and treatment of allergic diseases including allergic rhinitis, allergic asthma, atopic dermatitis and urticaria, and viral diseases including hepatitis B and AIDS, and it can elevate leukocyte, relieve physical fatigue, prevent and treat radiation injury, reducing toxic and side effects resulting from chemotherapy, and also improve the male sexual function.

The present invention is directed to studies on immuno-regulation and resistance against allergies.

Experiment 1

Studies on Immunomodulatory Effects According to the Present Invention

1. Materials and Methods
1.1 Experimental Animals

Kunming mice, each weighing 18 to 22 g, were purchased from the Laboratory Animal Center, Jiangxi University of Traditional Chinese Medicine, with a Certification Number: SCXK (Jiangxi)-2010-001.

1.2 Experimental Drugs

A TCM composition of the present invention (Radix Panacis Quinquefolii, Ganoderma, fermented Cordyceps sinensis powder, Flos Rosae Rugosae, and Rhizoma Anemarrhenae) was prepared as follows: a volatile oil was extracted from Flos Rosae Rugosae, and an aqueous solution obtained after distillation was collected in another container and stored until use; Radix Panacis Quinquefolii, Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; Ganoderma and fermented Cordyceps sinensis powder were mixed with the Flos Rosae Rugosae residue, Radix Panacis Quinquefolii residue and Rhizoma Anemarrhenae residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, and then granulated and dried; the Flos Rosae Rugosae volatile oil was sprayed uniformly to the granules, and mixed uniformly to prepare the final formulation.

1.3 Experimental Method
1.3.1 Animal Grouping:

The mice were randomly divided into 2 groups based on their body weights, i.e., a blank control group (Control, C) and a test drug group (the group on the TCM composition of the present invention, ZY), with ten animals per group.

1.3.2 Dosage Regime

The mice from the group of TCM composition of the present invention were given the composition at a dosage of 1.65 g crude drug/kg body weight. The drugs were prepared into corresponding concentrations before administration, and then intragastrically administrated at a dosing volume of 0.1 ml/10 g body weight. The blank control group was given an equal volume of distilled water. The intragastric administration was conducted once a day and continued for 30 days. Mice in both groups were fed with common feedstuff and allowed free access to feed and water.

1.3.3 Assay Indicators:

The phagocytic function of mice intraperitoneal macrophages; mice thymus coefficient and spleen index; carbon particles clearance capability; ConA-induced mice lymphocyte transformation test and NK cell activity measurement; serum hemolysin measurement and antibody-producing cell assay.

1.4 Statistic Methods

Quantitative data were presented in $\bar{x}\pm s$, and analyzed with the SPSS 10.0 software.

2 Results 2.1 Effects on Mice Thymus Coefficient and Spleen Index

As compared to the blank control group (C), the group on the TCM composition of the present invention (ZY) showed no significant effects on mice thymus system and spleen index ($P>0.05$). The results are shown in Table 1.

TABLE 1

| | Effects on mice thymus coefficient and spleen index ($\bar{x} \pm s$) | | | |
|---|---|---|---|---|
| Group No. | Dosage (g crude drug/kg) | Number of Animals | Thymus coefficient (mg/g) | Spleen index (mg/g) |
| C | — | 10 | 2.73 ± 0.34 | 3.51 ± 0.47 |
| ZY | 1.65 | 10 | 2.82 ± 0.49 | 3.62 ± 0.65 |

2.2 Effects on Lymphocyte Proliferation and Delayed Type Hypersensitivity in Mice As compared to the blank control group (C), the group on the TCM composition of the present invention (ZY) showed remarkable enhancement of ConA-induced spleen lymphocyte proliferation and the response to DNFB-induced DTH in mice ($p<0.05$ or $p<0.01$). The results are shown in Table 2.

TABLE 2

Effects on Immunity in mice ($\bar{x} \pm s$)

| Group No. | Dosage (g crude drugs/kg) | Number of animals | OD difference in ConA-induced lymphocyte proliferation | DNFB-induced DTH, weight difference between left and right ears (mg) |
|---|---|---|---|---|
| C | — | 10 | 0.052 ± 0.015 | 9.13 ± 0.75 |
| ZY | 1.65 | 10 | 0.089 ± 0.017** | 12.87 ± 01.13** |

Note:
*p < 0.05,
**p < 0.01 vs. blank control group.

2.3 Effects on Serum Hemolysin Level in Mice

As compared to the blank control group (C), the group on the TCM composition of the present invention (ZY) showed an effect of significantly increasing the serum hemolysin level in mice (p<0.05). The results are shown in Table 3.

TABLE 3

Effects on serum hemolysin level in mice ($\bar{x} \pm s$)

| Group No. | Dosage (g crude drugs/kg) | Number of animals | Serum hemolysin (sum of the antibody) |
|---|---|---|---|
| C | — | 10 | 52.15 ± 6.83 |
| ZY | 1.65 | 10 | 76.27 ± 8.15** |

Note:
*p < 0.05,
**p < 0.01 vs. blank control group.

2.4 Effects on the Phagocytic Function of Mice Intraperitoneal Macrophages

As compared to the blank control group (C), the group on the TCM composition of the present invention (ZY) showed an effect of significantly increasing the phagocytosis percentage of intraperitoneal macrophages in mice (p<0.01). The results are shown in Table 4.

TABLE 4

Effects on the phagocytic function of intraperitoneal macrophages ($\bar{x} \pm s$)

| Group No. | Dosage (g crude drugs/kg) | Number of animals | Phagocytosis percentage (%) |
|---|---|---|---|
| C | — | 10 | 27.37 ± 1.52 |
| ZY | 1.65 | 10 | 35.61 ± 2.43** |

Note:
*p < 0.05,
**p < 0.01 vs. blank control group.

2.5 Effects on Carbon Particles Clearance Function in Mice

As compared to the blank control group (C), the group on the TCM composition of the present invention (ZY) showed an effect of significantly increasing the phagocytic index (p<0.05 or p<0.01). The results are shown in Table 5.

TABLE 5

Effects on the carbon particle clearance function in mice ($\bar{x} \pm s$)

| Group No. | Dosage (g crude drugs/kg) | Number of animals | phagocytic index |
|---|---|---|---|
| C | — | 10 | 5.12 ± 0.23 |
| ZY | 1.65 | 10 | 7.42 ± 0.31** |

Note:
*p < 0.05,
**p < 0.01 vs. blank control group.

2.6 Effects on the Function of Antibody Producing Cells in Mice

As compared to the blank control group (C), the group on the TCM composition of the present invention (ZY) shows an effect of significantly increasing the number of hemolytic plaques (p<0.05, p<0.01). The results are shown in Table 6.

TABLE 6

Effects on function of antibody producing cells in mice ($\bar{x} \pm s$)

| Group No. | Dosage (g crude drugs/kg) | Number of animals | Number of hemolytic plaques (/$10^6$ spleen cells) |
|---|---|---|---|
| C | — | 10 | 232.7 ± 17.9 |
| ZY | 1.65 | 10 | 289.5 ± 21.7** |

Note:
*p < 0.05,
**p < 0.01 vs. blank control group.

2.7 Effects on NK Cell Activity in Mice

As compared to the blank control group (C), the group of TCM composition of the present invention (ZY) showed no significant effect on NK cell activity in mice (p>0.05). The results are shown in Table 7.

TABLE 7

Effects on NK cell activity in mice in each group ($\bar{x} \pm s$)

| Group No. | Dosage (g crude drugs/kg) | Number of animals | Cell activity (%) |
|---|---|---|---|
| C | — | 10 | 9.95 ± 2.41 |
| ZY | 1.65 | 10 | 10.03 ± 2.75** |

Note:
*p < 0.05,
**p < 0.01 vs. blank control group.

3. Conclusion

As demonstrated by the animal experimental studies, the TCM composition of the present invention (ZY) can increase ConA-induced spleen lymphocyte proliferation in mice, enhance the response to DNFB-induced DTH in mice, is effective in significantly increasing the serum hemolysin level in mice, increasing phagocytosis percentage of the intraperitoneal macrophage in mice and the carbon particle clearance function in mice, and can significantly increase the number of hemolytic plaques. According to the criteria for determining a function of enhancing immunity as provided in the *Technical Standards for Testing and Assessment of Health Food* (2003), the TCM composition of the present invention (ZY) is considered effective in enhancing immunity.

Experiment 2

Studies on Anti-Allergic Effects According to the Present Invention

1. Materials and Methods
1.1 Experimental Animals

Male ICR mice, each weighing 18 to 22 g, and male SD rats, each weighing 180 to 200 g, were purchased from the Laboratory Animal Center, Jiangxi University of Traditional Chinese Medicine, with a Certification Number: SCXK (Jiangxi)-2010-001.

1.2 Experimental Reagents

Ovalbumin and compound 48/80, products from Sigma Inc.; inactivated *Bordetella pertussis*, Ficoll and o-phthalaldehyde (OPT), products from Wako Inc.; disodium cromoglycate (DSCG), products from Biomol Inc.

1.3 Experimental Drugs

The same as in Experiment 1.

1.4 Animal Grouping and Dosage Regime

The mice were randomly divided into 2 groups, that is, a blank control group (Control, C), and a test drug group (the group on the TCM composition of the present invention, ZY), with ten animals per group. The mice from the group on the TCM composition of the present invention were given the composition at a dosage of 1.65 g crude drug/kg body weight. The drugs were prepared into corresponding concentrations before administration, and then intragastrically administrated at a dosing volume of 0.1 ml/10 g body weight. The blank control group was given an equal volume of distilled water. The intragastric administration was conducted once a day and continued for 10 days. Mice in both groups were fed with common feedstuff and allowed free access to feed and water.

1.5 Heterologous passive Cutaneous Anaphylaxis in Mice

A rat anti-ovalbumin antiserum was prepared according to a previous method described in the literature. 10 μl of a 5-fold dilution of the rat antiserum in physiological saline was injected into the left and right auricles of mice. After 48 h, 1% Evans blue in physiological saline (containing 1 mg/ml of ovalbumin) was intravenously injected at 10 ml/kg. After 30 min, the mice were sacrificed by exsanguination, both auricles were dissected and individually put into a 1N KOH solution for digestion overnight. The resultant was neutralized with 0.6 $NH_3PO_4$, and extracted with acetone. The extracts were measured for absorption at 610 nm, and the amount of Evans blue exudation in each ear was calculated by using a standard curve. The experimental data for each mouse was presented in average values of the data from left and right auricles. 1 h after the final administration, the experimental groups were challenged with ovalbumin 1.6 Compound 48/80 Induces Rat Peritoneal Mast Cells to Release Histamine The rats were sacrificed by exsanguination, and intraperitoneally injected with 20 ml Hanks' solution and gently massaged for 2 min. The peritoneal fluid was collected and mast cells were separated by Ficoll gradient centrifugation. The mast cells collected were washed 4 times with a phosphate buffer, and the mast cells obtained had a purity of about 91%. The cell concentration was adjusted to $2 \times 10^6$/ml. 0.9 ml mast cell suspension was pre-incubated at 37° C. for 10 min, into which 50 μl test sample was added. After incubation for 5 min, 50 μl compound 48/80 was added into the test tube (to a final concentration of 0.5 μg/ml), allowing a spontaneous release. After addition of 50 μl phosphate buffer in the test tube and incubation for 10 min, the test tube was transferred onto an ice bath for cooling, and the reaction was terminated. After centrifugation at 3000 r/min for 10 min, the supernatant (released amount) and the precipitate (residual amount) were measured by the fluorescence method for histamine contents. The histamine release rate was calculated as follows: release rate (%)=(released amount−spontaneous released amount)/(released amount+residual amount)×100%.

1.7 Statistic Processing

The experimental results were presented in $\bar{x} \pm s$, and the differences between groups were subjected to statistic processing with t test.

2 Results 2.1 Effects on Heterologous Passive Cutaneous Anaphylaxis in Mice

As indicated in Table 1, the group on the TCM composition of the present invention (ZY) showed reduced heterologous passive cutaneous anaphylaxis in mouse ears. The results are shown in Table 1.

TABLE 1

Effects on heterologous passive cutaneous anaphylaxis in mice ears ($\bar{x} \pm s$)

| Group No. | n | Dosage (g crude drugs/kg) | Amount of Evans blue exudation m/μg | Inhibition percentage (%) |
|---|---|---|---|---|
| C | 10 | — | 4.93 ± 1.21 | — |
| ZY | 10 | 1.65 | 1.52 ± 1.29* | 69.2 |

Note:
*p < 0.05,
**p < 0.01 vs. blank control group.

2.2 Effects on Histamine Release from Rat Peritoneal Mast Cells Induced by Compound 48/80

As compared to the blank control group (C), the group on the TCM composition of the present invention (ZY) showed a significant inhibition on the histamine release from rat peritoneal mast cells induced by Compound 48/80. The results are shown in Table 2.

TABLE 2

Effects on histamine release from rat peritoneal mast cells induced by Compound 48/80 ($\bar{x} \pm s$, n = 3)

| Group No. | Concentration C/μg/ml | Histamine release ratio (%) | Inhibition percentage (%) |
|---|---|---|---|
| C | — | 75.3 ± 5.7 | — |
| ZY | 100 | 35.6 ± 6.3** | 52.7 |
|  | 200 | 17.1 ± 5.9** | 77.3 |

Note:
*p < 0.05,
**p < 0.01 vs. blank control group.

In summary, the pathophysiology of allergy is a rapid anaphylactic response, namely the level of serum immunoglobulin E (IgE) in patients is abnormally elevated, resulting in high sensitivity to pollen, mold, dust mites, animal dander and other antigens. The group on the TCM composition of the present invention (ZY) showed substantially reduced heterologous passive cutaneous anaphylaxis in mice. As demonstrated in in vitro experiments, the group on the TCM composition of the present invention (ZY) showed an effect of significantly inhibiting histamine release from rat peritoneal mast cells induced by Compound 48/80, indicating that its anti-allergic activity may be associated with stabilization of the mast cell membrane and decrease in the release of allergy medium such as histamine.

Experiment 3

Studies on Anti-Radiation Effects According to the Present Invention

1 Materials 1.1 Experimental Animals

Male Kunming mice, each weighing 18 to 22 g, were purchased from the Laboratory Animal Center, Jiangxi University of traditional Chinese Medicine, with a Certification Number: SCXK (Jiangxi)-2010-001. After 3 days of acclimatization of the experimental animals to the environment, the experiment was conducted. The environment was kept at 20±2° C., with normal circadian rhythm, no glare and no noise stimulation. The animals were allowed free access to feed and water.

1.2 Experimental Drugs

A TCM composition of the present invention (Radix Panacis Quinquefolii, Ganoderma, fermented Cordyceps sinensis powder, Flos Rosae Rugosae, and Rhizoma Anemarrhenae) was prepared as follows: a volatile oil was extracted from Flos Rosae Rugosae, and an aqueous solution obtained after distillation was collected in another container and stored until use; Radix Panacis Quinquefolii and Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; Ganoderma and fermented Cordyceps sinensis powder were mixed with the Flos Rosae Rugosae residue, Radix Panacis Quinquefolii residue and Rhizoma Anemarrhenae residue, into which water in an amount of 6 to 12 folds was added, and decocted 2 to 3 times; the decoctions were combined with the above aqueous solution and subjected to filtration; the filtrate was concentrated to a relative density of 1.15 to 1.20 at 60° C., uniformly mixed with the above concentrate, and then granulated and dried; the Flos Rosae Rugosae volatile oil was sprayed uniformly to the granules, and mixed uniformly to prepare the final formulation. The mice were administrated at a dosage of 1.65 g crude drug/kg body weight. The drugs were prepared into corresponding concentrations before administration, and then intragastrically administrated at a dosing volume of 0.1 ml/10 g body weight. Mice in both groups were fed with common feedstuff and allowed free access to feed and water.

1.3 Experimental Instruments

Olympus Microscope (Olympus Corporation, Japan), Automatic biochemistry analyzer (Shimadzu, Japan), centrifuge (Beijing, China), UV spectrophotometer (UV-2401PC, Japan).

2 Method 2.1 Determination of the 30 d Survival Rate and Days Survived 30 mice were randomly divided into 3 groups: a normal control group, a model group, and a TCM composition group (TCM group) with 10 animals per group. The normal control group was not given any treatment, the model group was given distilled water, and the TCM composition group was intragastrically administrated with corresponding drugs once a day, with a dosing volume of 0.1 ml/10 g body weight. The mice in each group were continuously administrated for 21 d. 3 h after the final administration, the two groups other than the normal control group were subjected to systemic radiation once with 60Co γ irradiation, with an irradiation distance of 1.0 cm and a radiation dose of 7.5 Gy. After the irradiation, mice in each group were observed and recorded for survival status and body weight changes, and the average survival time of mice in each group and the 30 d survival rate were calculated.

2.2 Peripheral Blood WBC Count, Determination of DNA Content in Bone Marrow Cells, Thymus and Spleen Index Determination 60 mice were randomly divided into 10 groups by body weights, i.e., 2 normal control groups, 2 model groups and 2 TCM composition groups, with 10 animals per group. Amongst them, three groups were used for measurement of DNA content in bone marrow cells. The normal control groups were not given any treatment; the model groups were given distilled water, and the other two groups were intragastrically administrated with corresponding drugs, with the same administration method and volumes as before. The administration continued for 14 d. Except for the normal control groups, the other four groups were subjected to systemic radiation once with 60Co γ irradiation, with an irradiation distance of 1.0 cm and a total radiation dose of 3 Gy. 20 μl retinal blood was drawn from the mice before irradiation, 3 d after irradiation and 10 d after irradiation, respectively, a WBC dilution solution was added thereto and mixed, and the mixture was then transferred onto a blood count plate and the white blood cells (WBCs) were counted under a microscope. At the same time, the spleen and thymus were taken out and weighed to calculate the thymus and spleen index. 3 d after irradiation, the mice were sacrificed by cervical dislocation, complete femurs were dissected and any soft tissue attached thereon was removed. Bone marrow cells were extracted according to a method in the literature, and UV absorbance at 260 nm was measured using a UV spectrophotometer.

2.3 Statistic Processing

The experimental data were subjected to one-way variance analysis by using SPSS software. Leukocyte levels before and after irradiation were compared and subjected to statistic analysis with t test by using matching information.

3 Results 3.1 The general condition and 30 d survival rate of mice. After irradiation, the mice showed reduced appetite, decreased body weight, body curling, less activity, no smudginess such as feces and secretions on their skin and hair, with pale auricles and tails as well as a lower body surface temperature as compared to the normal group. The mice in the TCM composition group showed higher activity and food intake than mice in the model group. The number of survived mice in each group was counted twice a day. The results are shown in Table 1.

TABLE 1

Effects on 30d survival rate and survival period of mice having received 7.5 Gy irradiation

| Group No. | Dosage (g crude drugs/kg) | Number of animals | Number of the survived | survival rate (%) | survival period (d) |
|---|---|---|---|---|---|
| Normal group | — | 10 | 10 | 100 | 30.0 ± 0.0** |
| Model group | — | 10 | 0 | 0 | 7.23 ± 5.31 |
| TCM group | 1.65 | 10 | 3 | 30 | 15.65 ± 6.43** |

Note:
*p < 0.05,
**p < 0.01 vs. blank control group.

As indicated in Table 1, the TCM composition group showed a significantly increased 30 d survival rate of mice having received 7.5 Gy irradiation and a prolonged survival period of irradiated mice, demonstrating statistic significance as compared to model groups (P<0.01).

3.2 Effects on peripheral blood WBC count, DNA content in bone marrow cells, thymus and spleen index in mice. The results are shown in Tables 2 and 3.

TABLE 2

Effect of the anti-radiation TCM on the peripheral blood WBC count of mice before and after 3Gy irradiation ($\bar{x} \pm s$)

| Group No. | Dosage (g crude drugs/kg) | WBC count (×10$^5$/L) | | |
|---|---|---|---|---|
| | | Before radiation | 3 d after radiation | 10 d after radiation |
| Normal group | — | 8.97 ± 2.31 | 7.82 ± 2.35* | 7.79 ± 3.21* |
| Model group | — | 9.08 ± 2.86 | 2.15 ± 2.69 | 4.42 ± 2.53 |
| TCM group | 1.65 | 9.10 ± 2.72 | 5.27 ± 2.87* | 7.13 ± 2.47* |

Note:
*p < 0.05 vs. blank control group.

As indicated in Table 2, mice in each group showed no statistical difference in peripheral blood WBC count before radiation. 3 d after radiation, mice in the TCM composition group had a peripheral blood WBC count substantially higher than those of mice in the model group (given distilled water), which was statistically significant as compared to the model group. This indicates that the TCM composition has a certain protective effect on animals receiving low dose radiation.

TABLE 3

Effect on the thymus and spleen index, and DNA content in bone marrow cells in mice having received 3Gy irradiation ($\bar{x} \pm s$)

| Group No | Numbers of animal | Thymus index (mg/10 g) | spleen index (mg/10 g) | DNA content (OD) |
|---|---|---|---|---|
| Normal group | 10 | 21.51 ± 4.72* | 53.97 ± 11.13** | 0.23 ± 0.05* |
| Model group | 10 | 10.83 ± 5.37 | 32.79 ± 10.35 | 0.14 ± 0.07 |
| TCM group | 10 | 16.39 ± 5.12* | 46.16 ± 10.32* | 0.18 ± 0.06* |

Note:
*p < 0.05,
**p < 0.01 vs. blank control group.

As indicated in Table 3, the TCM composition groups showed increased thymus index and spleen index in the irradiated mice, and increased DNA contents in bone marrow cells in the irradiated mice, suggesting that the TCM composition is effective in repairing or protecting from the radiation damage to spleen and thymus and bone marrows caused by 60Co γ ray.

In summary, the TCM composition can improve 30 d-survival rate of mice receiving acute high-dose irradiation, improve the peripheral blood WBC count as well as thymus index and spleen index in mice receiving low-dose irradiation, and increase the DNA content in the bone marrow cells of mice irradiated, suggesting that the TCM composition is effective in repairing or protecting from the radiation damage to spleen and thymus and bone marrows caused by 60Co γ ray.

Experiment 4

Clinical Studies with Regard to the Present Invention

The present invention serves as a contract prescription of Jiangxi Medical College Hospital, which has been clinically used as a granule formulation for many years. Upon reviewing and analyzing 267 patients who used this prescription from January 2009 to January 2012, we summarized the results as below:

1. Distribution of cases: allergic rhinitis 41 cases, allergic asthma 28 cases, atopic dermatitis 27 cases, urticaria 21 cases, hepatitis B 35 cases, AIDS 13 cases, breast cancer chemotherapy 29 cases, leukopenia 23 cases, male sexual function decrease 29 cases, chronic fatigue syndrome 21 cases.
2. Age distribution: 21 to 68 years old
3. Gender distribution: male 143 cases, female 124 cases
4. Distribution of course of diseases: 3 months to 20 years
5. Treatment method: oral administration of 6 g, 3 times per day for one month, as a course of treatment.
6. Efficacy evaluation: efficacies were classified into three grades: (1) significantly effective: clinical symptoms almost or completely disappeared, and laboratory test indicators were close to normal or totally normal; (2) effective: clinical symptoms were alleviated, and laboratory test indicators were improved; (3) ineffective: clinical symptoms showed no obvious improvement, and laboratory test indicators were improved.

Efficacies in 267 patents clinically treated according to the present invention

| | Numbers of cases | Significantly effective | Effective | Ineffective | Overall percentage of effectiveness |
|---|---|---|---|---|---|
| Allergic rhinitis | 41 | 21 | 15 | 5 | 87.80 |
| Allergic asthma | 28 | 13 | 11 | 4 | 85.71 |
| Atopic dermatitis | 27 | 11 | 9 | 7 | 74.07 |
| Urticaria | 21 | 11 | 5 | 5 | 76.19 |
| Hepatitis B | 35 | 15 | 11 | 9 | 74.29 |
| AIDS | 13 | 5 | 4 | 4 | 69.23 |
| leukopenia | 23 | 10 | 8 | 5 | 75.26 |
| Breast cancer chemotherapy | 29 | 12 | 10 | 7 | 75.86 |
| Male sexual function decrease | 29 | 10 | 9 | 10 | 65.52 |
| Chronic fatigue syndrome | 21 | 10 | 5 | 6 | 71.43 |
| Total number of cases | 267 | 118 | 87 | 62 | 76.78 |

DETAILED DESCRIPTION OF THE INVENTION

The present invention will be described in details in the following Examples.

Example 1

Raw materials were weighed in the following parts by weight: 90 parts of Radix Panacis Quinquefolii, 90 parts of Ganoderma, 20 parts of fermented Cordyceps sinensis powder, 20 parts of Flos Rosae Rugosae, and 20 parts of Rhizoma Anemarrhenae.

Preparation method: the raw materials were weighed in the prescribed amounts; a volatile oil was extracted from Flos Rosae Rugosae, and an aqueous solution obtained after distillation was collected in another container and stored until use; Radix Panacis Quinquefolii and Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; *Ganoderma* and fermented *Cordyceps sinensis* powder were mixed with the Flos Rosae Rugosae residue, Radix Panacis Quinquefolii residue and Rhizoma Anemarrhenae residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, and then granulated and dried; the Flos Rosae Rugosae volatile oil was sprayed uniformly to the granules, and mixed uniformly to prepare the final formulation.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, is characterized in that the final formulation may be a granule, a tablet, a capsule, an electuary, a dripping pill, a pill, powder, a lozenge, a fluid extract, an extract, an injection, a syrup, or an oral liquid.

Example 2

Raw materials were weighed in the following parts by weight: 10 parts of Radix Panacis Quinquefolii, 10 parts of *Ganoderma*, 5 parts of fermented *Cordyceps sinensis* powder, 5 parts of Flos Rosae Rugosae, and 5 parts of Rhizoma Anemarrhenae.

Preparation method: the same as in Example 1.

Example 3

Raw materials were weighed in the following parts by weight: 30 parts of Radix Panacis Quinquefolii, 40 parts of *Ganoderma*, 20 parts of fermented *Cordyceps sinensis* powder, 25 parts of Flos Rosae Rugosae, and 16 parts of Rhizoma Anemarrhenae.

Preparation method: the same as that in Example 1.

Example 4

Raw materials were weighed in the following parts by weight: 10 parts of Radix Panacis Quinquefolii, 10 parts of *Ganoderma*, 5 parts of fermented *Cordyceps sinensis* powder, 5 parts of Flos Rosae Rugosae, 5 parts of Rhizoma Anemarrhenae, and 5 parts of Bulbus Lilii.

Preparation method: the raw materials were weighed in the prescribed amounts; a volatile oil was extracted from Flos Rosae Rugosae, and an aqueous solution obtained after distillation was collected in another container and stored until use; Radix Panacis Quinquefolii, Rhizoma Anemarrhenae and Bulbus Lilii were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; *Ganoderma* and fermented *Cordyceps sinensis* powder were mixed with the Flos Rosae Rugosae residue, Radix Panacis Quinquefolii residue, Rhizoma Anemarrhenae residue, and Bulbus Lilii residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, and then granulated and dried; the Flos Rosae Rugosae volatile oil was sprayed uniformly to the granules, and mixed uniformly to prepare the final formulation.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, is characterized in that the final formulation may be a granule, a tablet, a capsule, an electuary, a dripping pill, a pill, powder, a lozenge, a fluid extract, an extract, an injection, a syrup, or an oral liquid.

Example 5

Raw materials were weighed in the following parts by weight: 30 parts of Radix Panacis Quinquefolii, 40 parts of *Ganoderma*, 20 parts of fermented *Cordyceps sinensis* powder, 15 parts of Flos Rosae Rugosae, and 6 parts of Rhizoma Anemarrhenae.

Preparation method: the raw materials were weighed in the prescribed amounts, dried at 60 to 80° C., pulverized into fine powder of 40 to 100 meshes, and then encapsulated to obtain capsules; or made into water pills, dried at 60 to 80° C., and packed to obtain the final product.

Example 6

Raw materials were weighed in the following parts by weight: 30 parts of Radix Panacis Quinquefolii, 40 parts of *Ganoderma*, 20 parts of fermented *Cordyceps sinensis* powder, 15 parts of Flos Rosae Rugosae, and 16 parts of Rhizoma Anemarrhenae.

Preparation method: the raw materials were weighed in the prescribed amounts; a volatile oil is extracted from Flos Rosae Rugosae, an aqueous solution obtained after distillation is collected in another container, and the residue together with *Ganoderma* and fermented *Cordyceps sinensis* powder was decocted 2 times with addition of water in an amount of 6 to 12 folds; the decoctions were combined with the above aqueous solution and filtered, and the filtrate was concentrated to a relative density of 1.15 to 1.20 at 60° C.; the concentrate was uniformly mixed with a Radix Panacis Quinquefolii extract and a Rhizoma Anemarrhenae extract each in an amount equivalent to the prescribed amount, and then granulated and dried; the Flos Rosae Rugosae volatile oil was sprayed uniformly to the granules, and mixed uniformly to prepare the final formulation.

Example 7

Raw materials were weighed in the following parts by weight: 30 parts of Radix Panacis Quinquefolii, 40 parts of *Ganoderma*, 20 parts of fermented *Cordyceps sinensis* powder, 22 parts of Flos Rosae Rugosae, and 14 parts of Rhizoma Anemarrhenae.

Preparation method: extracts were weighed out each in an amount equivalent to the prescribed amounts of the crude drug, and then prepared into a final formulation with pharmaceutically acceptable carrier(s) or excipient(s) by a pharmaceutically conventional process.

Example 8

Raw materials were weighed in the following parts by weight: 30 parts of Radix Et Rhizoma Ginseng, 40 parts of *Ganoderma*, 20 parts of fermented *Cordyceps sinensis* powder, 22 parts of Flos Rosae Rugosae, and 15 parts of Rhizoma Anemarrhenae.

Preparation method: the raw materials were weighed in the prescribed amounts; a volatile oil was extracted from Flos Rosae Rugosae, and an aqueous solution obtained after distillation was collected in another container and stored until use; Radix Et Rhizoma Ginseng, Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; *Ganoderma* and fermented *Cordyceps sinensis* powder were mixed with the Flos Rosae Rugosae residue, Radix Et Rhizoma Ginseng residue and Rhizoma Anemarrhenae residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, and then granulated and dried; the Flos Rosae Rugosae volatile oil was sprayed uniformly to the granules, and mixed uniformly to prepare the final formulation.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, is characterized in that the final formulation may be a granule, a tablet, a capsule, an electuary, a dripping pill, a pill, powder, a lozenge, a fluid extract, an extract, an injection, a syrup, or an oral liquid.

Example 9

Raw materials were weighed in the following parts by weight: 30 parts of Radix Panacis Quinquefolii, 40 parts of *Ganoderma*, 20 parts of fermented *Cordyceps sinensis* powder, 25 parts of Flos Rosae Rugosae, and 16 parts of Rhizoma Anemarrhenae.

Preparation method: the raw materials were weighed in the prescribed amounts, soaked in added water for 40 min, and then decocted 3 times by heating with each decoction lasting for 2 h and a 10-fold amount of water added for each decoction; the three decoctions were combined and subjected to filtration, and the filtrate was concentrated to an appropriate amount; the concentrate was cooled and subjected to high-speed centrifugation to remove impurities; auxiliary agent(s) frequently used for oral liquid was added thereto and uniformly mixed, and an oral liquid was prepared.

Example 10

Raw materials were weighed in the following parts by weight: 30 parts of Radix Codonopsis, 40 parts of *Ganoderma*, 20 parts of fermented *Cordyceps sinensis* powder, 15 parts of Flos Rosae Rugosae, and 6 parts of Rhizoma Anemarrhenae.

Preparation method: the raw materials were weighed in the prescribed amounts; a volatile oil was extracted from Flos Rosae Rugosae, and an aqueous solution obtained after distillation was collected in another container and stored until use; Radix Codonopsis and Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; *Ganoderma* and fermented *Cordyceps sinensis* powder were mixed with the Flos Rosae Rugosae residue, Radix Codonopsis residue and Rhizoma Anemarrhenae residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, and then granulated and dried; the Flos Rosae Rugosae volatile oil was sprayed uniformly to the granules, and mixed uniformly to prepare the final formulation.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, is characterized in that the final formulation may be a granule, a tablet, a capsule, an electuary, a dripping pill, a pill, powder, a lozenge, a fluid extract, an extract, an injection, a syrup, or an oral liquid.

Example 11

Raw materials were weighed in the following parts by weight: 30 parts of Radix Pseudostellariae, 40 parts of *Ganoderma*, 20 parts of fermented *Cordyceps sinensis* powder, 15 parts of Flos Rosae Rugosae, and 6 parts of Rhizoma Anemarrhenae.

Preparation method: the raw materials were weighed in the prescribed amounts; a volatile oil was extracted from Flos Rosae Rugosae, and an aqueous solution obtained after distillation was collected in another container and stored until use; Radix Pseudostellariae and Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; *Ganoderma* and fermented *Cordyceps sinensis* powder were mixed with the Flos Rosae Rugosae residue, Radix Pseudostellariae residue and Rhizoma Anemarrhenae residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, and then granulated and dried; the Flos Rosae Rugosae volatile oil was sprayed uniformly to the granules, and mixed uniformly to prepare the final formulation.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, is characterized in that the final formulation may be a granule, a tablet, a capsule, an electuary, a dripping pill, a pill, powder, a lozenge, a fluid extract, an extract, an injection, a syrup, or an oral liquid.

Example 12

Raw materials were weighed in the following parts by weight: 30 parts of Radix Astragali, 40 parts of *Ganoderma*, 20 parts of fermented *Cordyceps sinensis* powder, 15 parts of Flos Rosae Rugosae, and 16 parts of Rhizoma Anemarrhenae.

Preparation method: the raw materials were weighed in the prescribed amounts; a volatile oil was extracted from Flos Rosae Rugosae, and an aqueous solution obtained after distillation was collected in another container and stored until use; Radix Astragali and Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; *Ganoderma* and fermented *Cordyceps sinensis* powder were mixed with the Flos Rosae Rugosae residue, Radix Astragali residue and Rhizoma Anemarrhenae residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, and then granulated and dried; the Flos Rosae Rugosae volatile oil was sprayed uniformly to the granules, and mixed uniformly to prepare the final formulation.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, is characterized in that the final formulation may be a granule, a tablet, a capsule, an electuary, a dripping pill, a pill, powder, a lozenge, a fluid extract, an extract, an injection, a syrup, or an oral liquid.

Example 13

Raw materials were weighed in the following parts by weight: 30 parts of Radix Et Rhizoma Ginseng, 40 parts of *Ganoderma*, 20 parts of fermented *Cordyceps sinensis* powder, 15 parts of Flos Rosae Rugosae, 6 parts of Rhizoma Anemarrhenae and 10 parts of *Ganoderma* spore powder.

Preparation method: the raw materials were weighed in the prescribed amounts; a volatile oil was extracted from Flos Rosae Rugosae, and an aqueous solution obtained after distillation was collected in another container and stored until use; Radix Et Rhizoma Ginseng and Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; *Ganoderma* and fermented *Cordyceps sinensis* powder were mixed with the Flos Rosae Rugosae residue, Radix Et Rhizoma Ginseng residue and Rhizoma Anemarrhenae residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, into which the *Ganoderma* spore powder was added, and then granulated and dried; the Flos Rosae Rugosae volatile oil was sprayed uniformly to the granules, and mixed uniformly to prepare the final formulation.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, is characterized in that the final formulation may be a granule, a tablet, a capsule, an electuary, a dripping pill, a pill, powder, a lozenge, a fluid extract, an extract, an injection, a syrup, or an oral liquid.

Example 14

Raw materials were weighed in the following parts by weight: 30 parts of Radix Et Rhizoma Ginseng, 40 parts of *Ganoderma*, 20 parts of fermented *Cordyceps sinensis* powder, 15 parts of Flos Rosae Rugosae, 10 parts of Rhizoma Anemarrhenae and 10 to 50 parts of *Ganoderma* spore oil.

Preparation method: the raw materials were weighed in the prescribed amounts; a volatile oil was extracted from Flos Rosae Rugosae, and an aqueous solution obtained after distillation was collected in another container and stored until use; Radix Et Rhizoma Ginseng and Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; *Ganoderma* and fermented *Cordyceps sinensis* powder were mixed with the Flos Rosae Rugosae residue, Radix Et Rhizoma Ginseng residue and Rhizoma Anemarrhenae residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, and then granulated and dried; the Flos Rosae Rugosae volatile oil was uniformly mixed with the *Ganoderma* spore oil, and sprayed uniformly to the granules to prepare the final formulation.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, is characterized in that the final formulation may be a granule, a tablet, a capsule, an electuary, a dripping pill, a pill, powder, a lozenge, a fluid extract, an extract, an injection, a syrup, or an oral liquid.

Example 15

Raw materials were weighed in the following parts by weight: 30 parts of Radix Et Rhizoma Ginseng, 40 parts of *Ganoderma*, 20 parts of fermented *Cordyceps sinensis* powder, 15 parts of Flos Rosae Rugosae, 6 parts of Rhizoma Anemarrhenae, 10 parts of Ganoderma spore powder, and 10 parts of *Ganoderma* spore oil.

Preparation method: the raw materials were weighed in the prescribed amounts; a volatile oil was extracted from Flos Rosae Rugosae, and an aqueous solution obtained after distillation was collected in another container and stored until use; Radix Et Rhizoma Ginseng and Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; *Ganoderma* and fermented *Cordyceps sinensis* powder were mixed with the Flos Rosae Rugosae residue, Radix Et Rhizoma Ginseng residue and Rhizoma Anemarrhenae residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, into which the *Ganoderma* spore powder was added, and then granulated and dried; the Flos Rosae Rugosae volatile oil was uniformly mixed with the *Ganoderma* spore oil, and sprayed uniformly to the granules to prepare the final formulation.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, is characterized in that the final formulation may be a granule, a tablet, a capsule, an electuary, a dripping pill, a pill, powder, a lozenge, a fluid extract, an extract, an injection, a syrup, or an oral liquid.

Example 16

Raw materials were weighed in the following parts by weight: 30 parts of Radix Panacis Quinquefolii, 40 parts of *Ganoderma,* 20 parts of *Cordyceps,* 25 parts of Flos Rosae Rugosae, and 16 parts of Rhizoma Anemarrhenae.

Preparation method: the raw materials were weighed in the prescribed amounts; a volatile oil was extracted from Flos Rosae Rugosae, and an aqueous solution obtained after distillation was collected in another container and stored until use; Radix Panacis Quinquefolii and Rhizoma Anemarrhenae were added into 60 to 80% ethanol and extracted twice, the ethanol solutions were combined and filtered, the filtrate was concentrated upon recovery of ethanol, and a concentrate having a relative density of 1.10 to 1.15 at 60° C. was obtained and stored until further use; *Ganoderma* and *Cordyceps* were mixed with the Flos Rosae Rugosae residue, Radix Panacis Quinquefolii residue and Rhizoma Anemarrhenae residue, into which water in an amount of 6 to 12 folds was added, and the mixture was decocted 2 to 3 times; the decoctions were combined with the above aqueous solution and subjected to filtration; the filtrate was concentrated to a relative density of 1.15 to 1.20 at 60° C., uniformly mixed with the above concentrate, and then granulated and dried; the Flos Rosae Rugosae volatile oil was sprayed uniformly to the granules, and mixed uniformly to prepare the final formulation.

The preparation method of the TCM composition as stated above, is characterized in that the final formulation may be in any dosage form manufactured with pharmaceutically acceptable carrier(s) or excipient(s) by a pharmaceutically conventional process.

The preparation method of the TCM composition as stated above, characterized in that the final formulation may be a granule, a tablet, a capsule, an electuary, a dripping pill, a pill, powder, a lozenge, a fluid extract, an extract, an injection, a syrup, or an oral liquid.

Example 17

Raw materials were weighed in the following parts by weight: 10 parts of Radix Panacis Quinquefolii extract, 14 parts of *Ganoderma* extract, 12 parts of *Cordyceps* extract, 10 parts of Flos Rosae Rugosae extract, and 11 parts of Rhizoma Anemarrhenae extract.

Preparation method: the raw materials were weighed in the prescribed amounts, dried at 60 to 80° C., and sieved to 40 to 100 meshes, and the fine powder was encapsulated to obtain capsules as the final product.

Example 18

Raw materials were weighed in the following parts by weight: 15 parts of Radix Panacis Quinquefolii saponin, 18 parts of *Ganoderma* polysaccharides, 13 parts of *Cordyceps* polysaccharides, 15 parts of Flos Rosae Rugosae flavone, and 18 parts of Rhizoma Anemarrhenae saponin Preparation method: the raw materials were weighed in the prescribed amounts, dried at 60 to 80° C., and sieved to 40 to 100 meshes, and the fine powder was encapsulated to obtain capsules as the final product.

Example 19

Raw materials were weighed in the following parts by weight: 15 parts of Radix Panacis Quinquefolii saponin, 10 parts of Radix Panacis Quinquefolii polysaccharides, 28 parts of *Ganoderma* triterpenoids, 13 parts of *Cordyceps* polysaccharides, 10 parts of *Cordyceps* amino acids, 17 parts of Flos Rosae Rugosae flavone, 11 parts of Rhizoma Anemarrhenae saponin and 8 parts of mangiferin.

Preparation method: the raw materials were weighed in the prescribed amounts, dried at 60 to 80° C., and sieved to 40 to 100 meshes, and the fine powder was encapsulated to obtain capsules as the final product.

What is claimed is:

1. A method of preventing or treating a medical condition comprising the step of administering to a subject in need thereof a traditional Chinese medicine composition,
   wherein the medical condition is selected from the group consisting of allergic rhinitis, allergic asthma, atopic dermatitis, urticaria, breast cancer chemotherapy, leukopenia, decreased male sexual function, chronic fatigue syndrome, radiation injury, a side effect from radiotherapy or chemotherapy, AIDS and hepatitis B, and
   wherein the composition comprises the following raw materials in parts by weight: 1 to 100 parts of Radix Panacis Quinquefolii, 1 to 100 parts of *Ganoderma,* 1 to 60 parts of fermented *Cordyceps sinensis* powder, 1 to 60 parts of Flos Rosae Rugosae, and 1 to 60 parts of Rhizoma Anemarrhenae, or extracts thereof in amounts equivalent to the amounts of the raw materials.

2. The method of claim 1, wherein the medical condition is radiation injury.

3. The method of claim 1, wherein the medical condition is a side effect from radiotherapy or chemotherapy.

4. The method of claim 1, wherein the medical condition is decreased male sexual function.

5. The method of claim 1, wherein the medical condition is allergic rhinitis.

6. The method of claim 1, wherein the medical condition is allergic asthma.

7. The method of claim 1, wherein the medical condition is atopic dermatitis.

8. The method of claim 7, wherein the composition further comprises 10 to 50 parts of *Ganoderma* spore powder and/or 10 to 50 parts *Ganoderma* spore oil.

9. The method of claim 1, wherein the medical condition is urticaria.

10. The method of claim 1, wherein the medical condition is breast cancer chemotherapy.

11. The method of claim 1, wherein the medical condition is leukopenia.

12. The method of claim 1, wherein the medical condition is chronic fatigue syndrome.

13. The method of claim 1, wherein the medical condition is hepatitis B.

14. The method of claim 1, wherein the medical condition is AIDS.

15. The method of claim 1, wherein the composition further comprises 10 to 50 parts of Bulbus Lilii or an extract thereof in an equivalent amount.

16. The method of claim 1, wherein the raw materials in parts by weight are: 10 to 90 parts of Radix Panacis Quinquefolii, 10 to 90 parts of *Ganoderma*, 5 to 50 parts of fermented *Cordyceps sinensis* powder, 5 to 50 parts of Flos Rosae Rugosae, and 5 to 50 parts of Rhizoma Anemarrhenae.

17. The method of claim 1, wherein the raw materials in parts by weight are: 30 parts of Radix Panacis Quinquefolii, 40 parts of *Ganoderma*, 20 parts of fermented *Cordyceps sinensis* powder, 25 parts of Flos Rosae Rugosae, and 16 parts of Rhizoma Anemarrhenae.

18. The method of claim 1, wherein the fermented *Cordyceps sinensis* powder is prepared through biological fermentation, and the species from which the fermented *Cordyceps sinensis* powder is derived is selected from the group consisting of *Paecilomyces hepiali, Mortiscrslla hepialid, Synnematium sinensis, Gliocladium roseum, Mortierella* sp., *Cephalosporium sinensis*, and *Hirsutella sinensis*.

* * * * *